United States Patent
Namatame et al.

(10) Patent No.: US 9,783,774 B2
(45) Date of Patent: Oct. 10, 2017

(54) CELL CULTURE CONTROL SYSTEM, CELL CULTURE CONTROL METHOD, AND NON-TRANSITORY COMPUTER READABLE STORAGE MEDIUM

(71) Applicant: YOKOGAWA ELECTRIC CORPORATION, Musashino-shi, Tokyo (JP)

(72) Inventors: Tetsushi Namatame, Tokyo (JP); Souichirou Shimoda, Tokyo (JP); Yasuyuki Suzuki, Tokyo (JP); Fumiaki Izaki, Tokyo (JP)

(73) Assignee: Yokogawa Electric Corporation, Musashino-shi, Tokyo (JP)

( * ) Notice: Subject to any disclaimer, the term of this patent is extended or adjusted under 35 U.S.C. 154(b) by 25 days.

(21) Appl. No.: 14/700,301

(22) Filed: Apr. 30, 2015

(65) Prior Publication Data

US 2015/0329817 A1 Nov. 19, 2015

(30) Foreign Application Priority Data

May 19, 2014 (JP) ................. 2014-103719

(51) Int. Cl.
*C12M 1/34* (2006.01)
*C12M 1/36* (2006.01)

(52) U.S. Cl.
CPC ............ *C12M 41/12* (2013.01); *C12M 41/00* (2013.01); *C12M 41/26* (2013.01); *C12M 41/32* (2013.01);
(Continued)

(58) Field of Classification Search
CPC ...... C12M 41/12; C12M 41/00; C12M 41/38; C12M 41/48; C12M 41/26; C12M 41/40; C12M 41/32
See application file for complete search history.

(56) References Cited

U.S. PATENT DOCUMENTS

2007/0207538 A1    9/2007  Amano
2008/0167852 A1*   7/2008  Bartee ............... C12P 7/06
                                                        703/11
(Continued)

FOREIGN PATENT DOCUMENTS

EP    0661380 A2    7/1995
JP    7184634 A     7/1995
(Continued)

OTHER PUBLICATIONS

Wong et al., "Impact of Dynamic Online Fed-Batch Strategies on Metabolism, Productivity and N-Glycosylation Quality in CHO Cell Cultures," Biotechnology and Bioengineering, Willey Periodicals, Inc., Jan. 20, 2005, vol. 89, No. 2, XP009142862, pp. 164-177, 14 pages total.

(Continued)

*Primary Examiner* — Shogo Sasaki
(74) *Attorney, Agent, or Firm* — Sughrue Mion, PLLC (57) ABSTRACT

A cell culture control system includes a controller configured to control parameters of a culture fluid which exists in a processor in accordance with a control value which is preliminarily set, a generator configured to generate time-series data by using a concentration value of the metabolic substances in the culture fluid, the concentration value of the metabolic substances being detected by a sensor, an extractor configured to extract a characteristic point of the time-series data generated by the generator, and a control value setter configured to change the control value in accordance with the characteristic point extracted by the extractor.

18 Claims, 5 Drawing Sheets

(52) U.S. Cl.
CPC ............ *C12M 41/38* (2013.01); *C12M 41/40* (2013.01); *C12M 41/48* (2013.01)

(56) References Cited

U.S. PATENT DOCUMENTS

| | | | |
|---|---|---|---|
| 2009/0048816 A1* | 2/2009 | Srinivasa | C12M 41/48 703/11 |
| 2009/0104594 A1 | 4/2009 | Webb | |
| 2010/0081122 A1 | 4/2010 | Shibuya et al. | |
| 2010/0193358 A1* | 8/2010 | Hamada | C12Q 1/18 204/547 |
| 2012/0310413 A1* | 12/2012 | Bluck | G06N 99/005 700/266 |

FOREIGN PATENT DOCUMENTS

| | | |
|---|---|---|
| JP | 2003-235544 A | 8/2003 |
| JP | 2007-202500 A | 8/2007 |
| JP | 2008-43301 A | 2/2008 |
| JP | 2008-178344 A | 8/2008 |
| JP | 2010-81805 A | 4/2010 |
| JP | 2010-81809 A | 4/2010 |
| JP | 201192041 A | 5/2011 |
| JP | 2011135826 A | 7/2011 |
| JP | 2013101111 A | 5/2013 |
| WO | 2007/052653 A1 | 5/2007 |
| WO | 2008/010005 A1 | 1/2008 |
| WO | 2014006551 A1 | 1/2014 |

OTHER PUBLICATIONS

Woo Suk Ahn et al., "Metabolic flux analysis of CHO cells at growth and non-growth phases using isotopic tracers and mass spectrometry", Metabolic Engineering, 2011, pp. 598-609, vol. 13.
Wei-Shou Hu, "Cell Culture Bioprocess Engineering", pp. 236, 2012.
Moon Sue Lee et al., "Effect of hypoosmotic pressure on cell growth and antibody production in recombinant Chinese hamster ovary cell culture", Cytotechnology, 2001, pp. 61-69, vol. 36.
Danny Chee Furng Wong, et al., "Impact of Dynamic Online Fed-Batch Strategies on Metabolism, Productivity and N-Glycosylation Quality in CHO Cell Cultures", Biotechnology and Bioengineering, Jan. 20, 2005, pp. 164-177, vol. 89, No. 2.
Takeshi Omasa et al., "The enhancement of specific antibody production rate in glucose- and glutamine-controlled fed-batch culture", Cytotechnology, 1992, pp. 75-84, vol. 8.
Duan Shen et al., "Transcriptomic Responses to Sodium Chloride-Induced Osmotic Stress: A Study of Industrial Fed-Batch CHO Cell Cultures", Biotechnol. Prog., 2010, pp. 1104-1115, vol. 26, No. 4.
Young Kue Han et al., "Hyperosmotic Stress Induces Autophagy and Apoptosis in Recombinant Chinese Hamster Ovary Cell Culture", Biotechnology and Bioengineering, Apr. 15, 2010, pp. 1187-1192, vol. 105, No. 6.
Wong et al., "Impact of Dynamic Online Fed-Batch Strategies on Metabolism, Productivity and N-Glycosylation Quality in CHO Cell Cultures," Biotechnology and Bioengineering, Wiley Periodicals, Inc., Jan. 20, 2005, vol. 89, No. 2, XP009142862, pp. 164-177, 14 pages total.

* cited by examiner

CELL CULTURE CONTROL SYSTEM, CELL CULTURE CONTROL METHOD, AND NON-TRANSITORY COMPUTER READABLE STORAGE MEDIUM

BACKGROUND OF THE INVENTION

Field of the Invention

The disclosure relates to a cell culture control system, a cell culture control method, and a non-transitory computer readable storage medium.

Priority is claimed on Japanese Patent Application No. 2014-103719, filed May 19, 2014, the contents of which are incorporated herein by reference.

Description of Related Art

A production of a biological medicine, which uses high molecular biological molecule, includes a culture process and a purification process. In the culture process, objective substances are produced by biological response. In the purification process, foreign substances which are produced in the culture process are removed, and a purity of the objective substances is improved. In the culture process of an antibody medicine which represents the biological medicine, animal cells such as CHO cells are mainly used. However, the animal cells are easily affected by a culture environment. For the reason, in a case where the culture environment is not kept appropriately, a quantity and a quality of the objective products are affected.

In comparison with a chemical medicine, the production of the biological medicine is easily affected by a process, and it is difficult to produce the biological medicine stably. Therefore, developing a production technology for implementing an efficient and stable production is desired strongly.

Causes for degradation of the culture environment are such as mechanical stress by agitation and gas flow, depletion of nutrient and oxygen, accumulation of waste material such as lactic acid and ammonia produced by the cells. For the reason, a production method, which controls basic environmental factors such as dissolved oxygen concentration, pH, temperature, and agitation speed of a culture fluid, and supplies materials which the cells require while culturing, is used. The supplied materials are such as nutrient components included in the culture fluid and augmenting agents for improving growth rate or production rate of the cells.

A culture method for supplying materials while culturing is such as a continuous culture, a perfusion culture, and a fed-batch culture. In the continuous culture and the perfusion culture, the culture environment can be easily kept constant, and stable production can be conducted. However, there is a risk that a contamination remains after the contamination is generated, and there is a disadvantage of high cost caused by large consumption of the culture fluid.

On the other hand, in the fed-batch culture, although a culture fluid for feeding (feed agent) is added into a tank, the culture fluid for feeding is not removed from the tank. The fed-batch culture is a culture method for densifying the cells by attenuating the waste material such as lactic acid and ammonia which are harmful for the cells. Also, the fed-batch culture is a majority culture method in a current commercial production. For example, the fed-batch culture is described in Japanese Unexamined Patent Application Publication No. 2003-235544, Japanese Unexamined Patent Application Publication No. 2008-178344, and Danny Chee Furng Wong, et al., Biotechnology and Bioengineering, VOL. 89, NO. 2, Jan. 20, 2005: 164-177.

In the Japanese Unexamined Patent Application Publication No. 2003-235544, a culture method for calculating factors such as a specific growth rate and a specific production rate which are important for culturing the cells is described. The factors are calculated from online monitoring values (for example, pH and temperature) and analysis values obtained by sampling a cell concentration and cell metabolism components. The cells are cultured while monitoring a predicted value and an actual value of them.

In the Japanese Unexamined Patent Application Publication No. 2008-178344, a culture method for calculating a variation amount of a living cell number and a reduction amount of culture medium components. Components which are included in the culture fluid are added in accordance with a relation between the variation amount of a living cell and the reduction amount of culture medium components, and the components which are included in the culture fluid are kept constant.

In the Japanese Unexamined Patent Application Publication No. 2003-235544 and the Japanese Unexamined Patent Application Publication No. 2008-178344, the culture methods for culturing the cells while keeping the culture environment in a suitable condition are described. However, there is a need for the both methods to analyze the culture fluid by sampling.

In Danny Chee Furng Wong, et al., Biotechnology and Bioengineering, VOL. 89, NO. 2, Jan. 20, 2005: 164-177, an advantageous effect such as a production rate improvement caused by a nutrient source low concentration control is described. Also, it is described that variations of their concentration affect a glycosylation pattern which relates to antibody quality.

However, in the analysis of the components, which is necessary for the cell culture methods described in the Japanese Unexamined Patent Application Publication No. 2003-235544 and the Japanese Unexamined Patent Application Publication No. 2008-178344, about one hour is required, the contamination risk is increased, and there is a limitation of man-hour. For the reason, the analysis is generally performed once daily. Therefore, the culture condition (for example, the concentration of the each component) cannot be monitored at short intervals.

When the cells are cultured, for example, it is difficult to control to keep "substrate concentration" constant. Therefore, it is difficult to keep the concentration range (about ±0.1 mM) described in Danny Chee Furng Wong, et al., Biotechnology and Bioengineering, VOL. 89, NO. 2, Jan. 20, 2005: 164-177.

SUMMARY

A cell culture control system may include a controller configured to control parameters of a culture fluid which exists in a processor in accordance with a control value which is preliminarily set, a generator configured to generate time-series data by using a concentration value of the metabolic substances in the culture fluid, the concentration value of the metabolic substances being detected by a sensor, an extractor configured to extract a characteristic point of the time-series data generated by the generator, and a control value setter configured to change the control value in accordance with the characteristic point extracted by the extractor.

Further features and aspects of the present disclosure will become apparent from the following detailed description of exemplary embodiments with reference to the attached drawings.

DETAILED DESCRIPTION OF THE EMBODIMENTS

The embodiments of the present invention will be now described herein with reference to illustrative preferred embodiments. Those skilled in the art will recognize that many alternative preferred embodiments can be accomplished using the teaching of the present invention and that the present invention is not limited to the preferred embodiments illustrated herein for explanatory purposes.

An aspect of the present invention is to provide a cell culture control system, a cell culture control method, and a non-transitory computer readable storage medium which can control an operation output value of a basic environmental factor and a timing when agents such as nutrient sources, feed agents, and augmenting agents are added, so as to establish the culture environment in accordance with cell conditions (for example, a specific growth rate, a specific production rate, and a specific consumption rate, and so on).

The cell culture control system, the cell culture control method, and a non-transitory computer readable storage medium of the present embodiment will be described below with reference to drawings.

Figure 1:
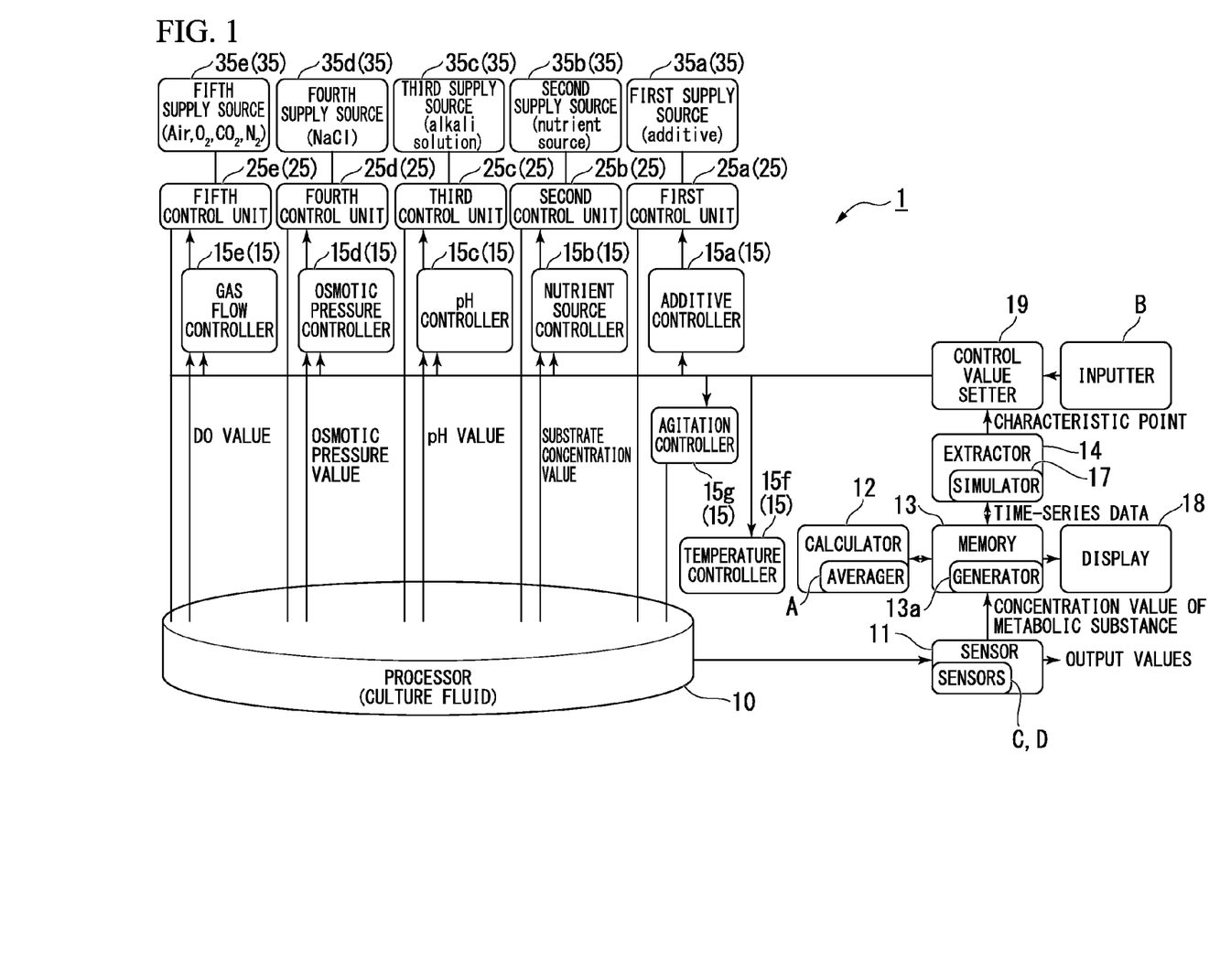
FIG. 1 is a drawing illustrating an example of a block diagram of the cell culture control system.

FIG. 1 is a drawing illustrating an example of a block diagram of the cell culture control system. The cell culture control system 1 of the present embodiment is equipped with a processor 10 (for example, a bioreactor, a treatment tank, and another tank) and a controller 15. The processor 10 cultures cells in the culture fluid. The controller 15 controls physical and chemical parameters of the culture fluid in the processor 10 in accordance with a predetermined control value (hereinafter "target value"). The cell culture control system 1 is also equipped with a sensor 11, a memory 13, an extractor 14, and a control value setter 19. The sensor 11 detects a concentration value of metabolic substances in the culture fluid. The memory 13 is equipped with a generator 13a. The generator 13a generates time-series data in accordance with outputs from the sensor 11. The memory 13 stores the generated time-series data. The extractor 14 extracts a characteristic point of the time-series data. The control value setter 19 changes the control value (the target value) in accordance with an output from the extractor 14.

By these configuration described above, the controller 15 which is a part of the cell culture control system 1 can control the physical and chemical parameters of the culture fluid in the processor 10 in accordance with the predetermined control value (the target value). Therefore, by the present embodiment, a substrate concentration can be controlled in accordance with the cell conditions. In the culture fluid existing in the processor 10, excess accumulation of the waste material is suppressed. As the result, the cell culture control system 1 can densify the cells and make the concentration of the products be high by keeping the concentration suitable for producing the products. Further, the cell culture control system 1 can improve productivity.

The control value is provided by the generator 13a which generates the time-series data in accordance with the output from the sensor 11, the memory 13 which stores the generated time-series data, the extractor 14 which extracts the characteristic point of the time-series data, and the control value setter 19 which changes the control value (the target value) in accordance with the output from the extractor 14.

Detail configurations of the cell culture control system 1 will be described below with reference to FIG. 1.

<Sensor 11>

The sensor 11 has a function of monitoring the nutrient components in the culture fluid which exists in the processor 10 and the metabolic components of the cells. The sensor 11 is connected to the processor 10 (hereinafter, also called as a bioreactor, a treatment tank, and another tank). In a case of in-line monitoring, a sensor function part (not shown) of the sensor 11 is used while being directly inserted into the processor 10.

The sensor 11 has functions for calculating a cell density (including a survival rate) in the culture fluid, a concentration value of the metabolic substances, a concentration value of the nutrient sources, a pH value, a temperature value, and an osmotic pressure value. The metabolic substances include lactic acid and ammonia. The nutrient sources include glucose and glutamine. In the sensor 11, the temperature, the pH, and the dissolved oxygen concentration are detected by each of sensor function parts (not shown) which are different each other.

The sensor 11 detects the cell density by performing image recognition with respect to stained cells or using an immersion-type capacitance sensor C (illustrated in the sensor 11 shown in FIG. 1). The "image recognition with respect to stained cells" is a method of staining the cells by mixing trypan blue and the cell a culture fluid, inserting the mixed fluid into a mount (having a fixed space) made of glass or plastic, performing image processing, counting a number of living cells which are not stained and a number of dead cells which are stained blue, and automatically calculating the cell density and the survival rate. Instead of the counting method, the number of the living cells and the number of the dead cells may be counted manually by using a counting chamber. As the measurement method of the cell density, NIRS (near-infrared (NIR) spectroscopy) may be used.

The concentration value of the metabolic substances and the concentration value of the nutrient sources are detected by a sensor D (illustrated in the sensor 11 shown in FIG. 1) such as a sensor of the NIRS, a sensor of an enzymatic electrode method, or a sensor of a colorimetric method. The osmotic pressure is detected by the sensor of the NIRS. For example, the sensor of the NIRS detects the osmotic pressure every few minutes.

The sensor of the NIRS preliminarily creates a standard curve which associates an each component value with an absorbance, and analyzes many components at a single measurement. The number of the cells and the osmotic pressure can be analyzed by using baseline wander and an absorption range of water. The single measurement takes about a few minutes.

<Memory 13>

The memory 13 is connected to an output side of the sensor 11. The generator 13a in the memory 13 generates the time-series data by using the output from the sensor 11. The memory 13 stores the created time-series data. For example, the memory 13 creates the time-series data every few minutes. The memory 13 is connected to an output side of the calculator 12. The generator 13a generates time-series data in accordance with the output from the calculator 12. The memory 13 stores the generated time-series data.

Further, the memory 13 is connected to the extractor 14. The memory 13 stores a characteristic point in accordance with an output from the extractor 14. The output from the extractor 14 is such as the concentration value of the metabolic substances, the specific production rate value of the metabolic substances, the concentration value of the nutrient sources, the specific consumption rate value of the nutrient sources, the pH value, the temperature value, the concentration value of the dissolved oxygen, the specific consumption rate value of the dissolved oxygen, the osmotic pressure value, and so on. The generator 13a generates the time-series data of them. The memory 13 stores the generated time-series data. The memory 13 also stores the characteristic points obtained in accordance with these time-series data.

<Calculator 12>

The calculator 12 is connected to the memory 13. The calculator 12 connected to the sensor 11 via the memory 13. The calculator 12 calculates a specific rate (a rate of each parameter per one cell). The specific rate is such as the specific growth rate, the specific consumption rate of the nutrient sources, and the specific production rate of the metabolic substances.

As shown in the formula (1) described below, the specific growth rate μ is related to a concentration Xt of all the cells and a concentration Xv of the living cells. Therefore, the calculator 12 can calculate the specific growth rate μ by using a formula "the specific growth rate $\mu=(1/Xv)\times(dXt/dt)$".

(Formula 1)

$$\frac{dX_t}{dt} = \mu X_v \quad (1)$$

$X_t$: CONCENTRATION OF ALL CELLS
$X_v$: CONCENTRATION OF LIVING CELLS
μ: SPECIFIC GROWTH RATE

As shown in the formula (2) described below, the specific consumption rate vGluc of the glucose is related to the concentration Xv of the living cells. Therefore, the calculator 12 can calculate the specific consumption rate vGluc by using a formula "the specific consumption rate $vGluc=(-1/Xv)\times(dGluc/dt)$". The specific consumption rate vGluc of the glucose is an example of the specific consumption rate of the nutrient sources. The calculator 12 also calculates a specific consumption rate of the glutamine by using the same method of calculating the specific consumption rate of the glucose.

(Formula 2)

$$\frac{dGluc}{dt} = -v_{Gluc}X_v \quad (2)$$

Gluc: CONCENTRATION OF GLUCOSE
$v_{Gluc}$: SPECIFIC CONSUMPTION RATE OF GLUCOSE

As shown in the formula (3) described below, the specific production rate ρLac of the lactic acid is related to the concentration Xv of the living cells. Therefore, the calculator 12 can calculate the specific production rate ρLac of the lactic acid by using a formula "the specific production rate $\rho Lac=(1/Xv)\times(dLac/dt)$". The specific production rate ρLac of the lactic acid is an example of the specific production rate of the metabolic substances. The calculator 12 also calculates a specific production rate of the ammonia by using the same method of calculating the specific production rate of the lactic acid.

(Formula 3)

$$\frac{dLac}{dt} = \rho_{Lac}X_v \quad (3)$$

Lac: CONCENTRATION OF LACTIC ACID
$\rho_{Lac}$: SPECIFIC PRODUCTION RATE OF LACTIC ACID <Averager A>

An averager A is included in the calculator 12. The averager A is connected to the memory 13. The averager A connected to the sensor 11 via the memory 13. The averager A calculates a representative value by averaging the output from the sensor 11 in a predetermined period. Further, the averager A also calculates a rate component of the representative value.

<Extractor 14>

Figure 6:
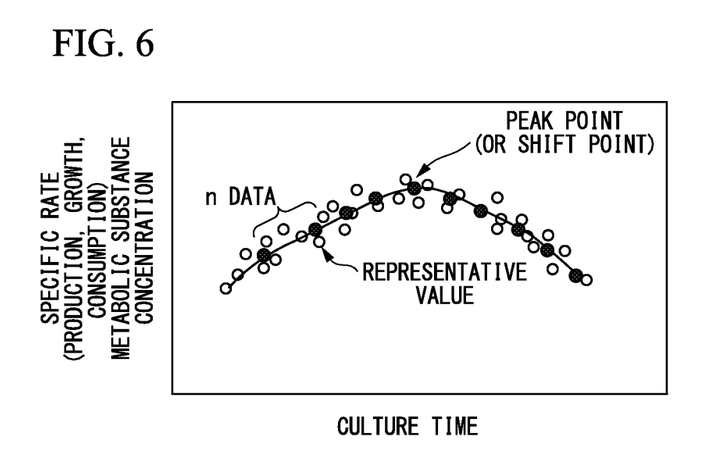
FIG. 6 is a graph illustrating a relation between the culture time and the specific rate or the concentration value of the metabolic substance.

The extractor 14 is connected to the memory 13. The extractor 14 extracts the characteristic point (for example, a peak point and a shift point) of the time-series data stored in the memory 13. For example, as shown in FIG. 6, the extractor 14 sequentially calculates the representative values of n data, and stores the calculated representative values in the memory 13. Because the each concentration value and the calculated value include some variability, the extractor 14 calculates the representative value such as an average value and a center value in accordance with the most recent n data.

Specifically, the extractor 14 extracts a characteristic point of the time-series data of the concentration value of the metabolic substances. The extractor 14 also extracts a characteristic point of the time-series data of the specific production rate of the lactic acid. For example, a shift timing of the cell condition is determined in accordance with flow-charts shown in FIG. 3 and FIG. 4 which will be described later. The extractor 14 extracts a time when a sign of the time-series data of the specific rate varies. For example, the extractor 14 extracts a time (shift point) when the sign of the specific production rate of the lactic acid is shifted from positive to negative. The extractor 14 may extract increase and decrease of an inclination angle of the time-series data in a period when the sign of the time-series data of the specific rate does not vary (for example, a period of increasing tendency, a period of decreasing tendency, and a period of approximately constant).

Figure 3:
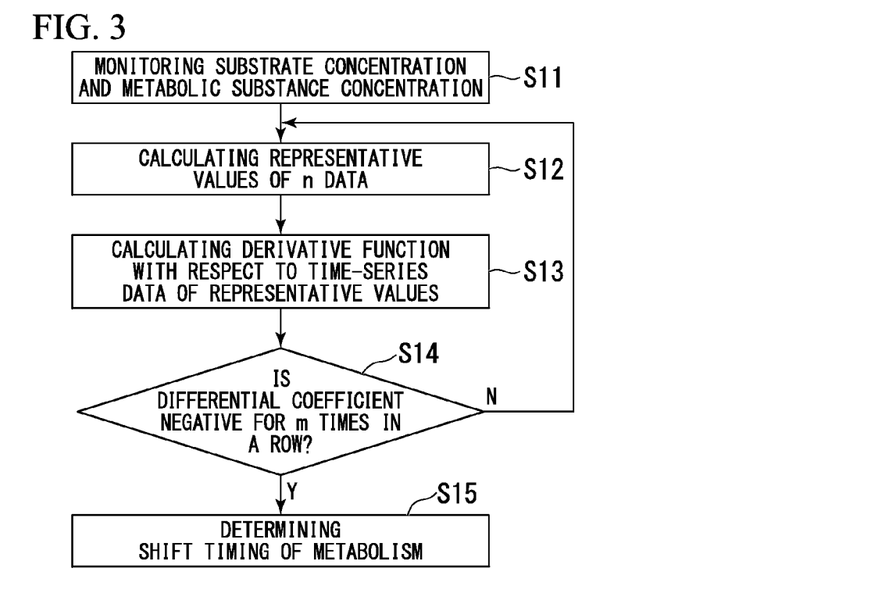
FIG. 3 is an example of a flowchart of determining a shift timing of metabolism.

FIG. 3 is an example of a flowchart of determining a shift timing of the metabolism. In FIG. 3, the shift timing of the metabolism is determined as the shift timing of the cell condition. First, the extractor 14 monitors the substrate concentration and the metabolic substance concentration (step S11). Next, the extractor 14 calculates the representative values of n data (step S12). Thereafter, the extractor 14 calculates a derivative function with respect to the time-series data of the representative values (step S13).

Next, the extractor 14 determines whether or not a differential coefficient of the derivative function is negative for m times in a row (step S14). In a case where the differential coefficient of the derivative function is not negative for m times in a row (step S14: NO), processing returns to step S12. In a case where the differential coefficient of the derivative function is negative for m times in a row (step S14: YES), the extractor 14 determines the shift timing of the metabolism as the shift timing of the cell condition (step S15).

Figure 4:
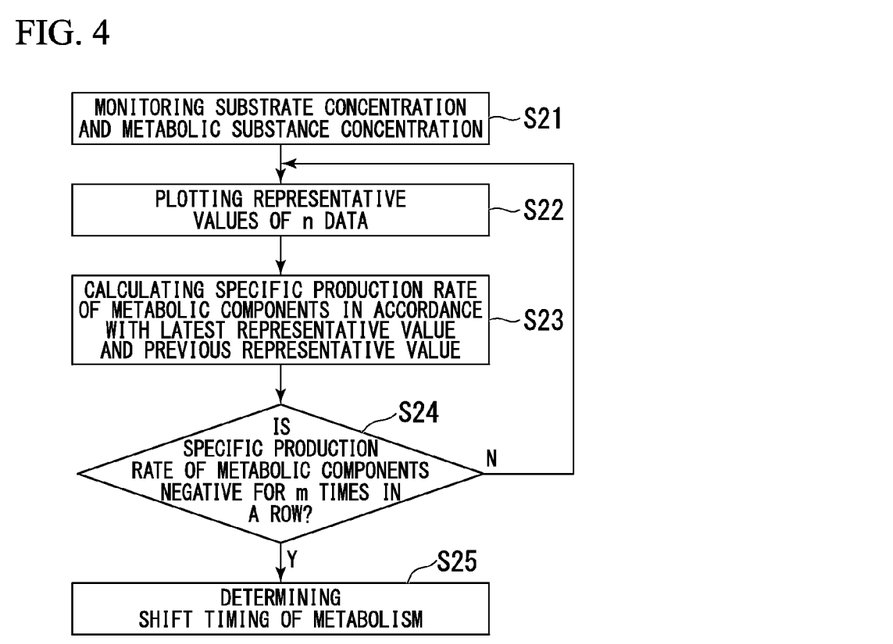
FIG. 4 is another example of a flowchart of determining a shift timing of metabolism.

FIG. 4 is another example of a flowchart of determining a shift timing of the metabolism. In FIG. 4, the shift timing of the metabolism is determined as the shift timing of the cell condition. First, the extractor 14 monitors the substrate concentration and the metabolic substance concentration (step S21). Next, the extractor 14 plots the representative values of n data (step S22). Thereafter, the extractor 14 calculates the specific production rate of the metabolic components in accordance with a latest representative value and a previous representative value (step S23).

Next, the extractor 14 determines whether or not the specific production rate of the metabolic components is negative for m times in a row (step S24). In a case where the specific production rate of the metabolic components is not negative for m times in a row (step S24: NO), processing returns to step S2. In a case where the specific production rate of the metabolic components is negative for m times in a row (step S24: YES), the extractor 14 determines the shift timing of the metabolism as the shift timing of the cell condition (step S25).

<Simulator 17>

A simulator 17 is included in the extractor 14. The simulator 17 is connected to the memory 13. The simulator 17 calculates time-series data which are from a few hours later to one day later in accordance with the time-series data stored in the memory 13 by using a physical model or a chemical model (a model based on a first principle such as material balance and energy balance) and a biology model (a model based on experiences and phenomena of biology). The time-series data calculated at this time is "a predicted value of the time-series data of the concentration value of the nutrient sources in the culture fluid, the temperature value, the pH value, the concentration value of the dissolved oxygen, the osmotic pressure, and the concentration value of the metabolic substances".

In a case where the simulator 17 uses the predicted value, for example, the simulator 17 determines the shift timing of the cell condition in accordance with a flowchart shown in FIG. 5 which will be described later. The simulator 17 can determine the shift point of the cell condition in accordance with not only an aging variation of the lactic acid, but also an aging variation of the each specific rate of the substrate and the metabolic substances. Parameters which are used for calculating the shift point of the cell condition are preliminarily determined by conducting a preliminary experiment. The simulator 17 outputs information indicating the shift point of the cell condition to an additive controller 15a, a nutrient source controller 15b, a pH controller 15c, an osmotic pressure controller 15d, a gas flow controller 15e, a temperature controller 15f, and an agitation controller 15g. These controllers 15a to 15g are included in the controller 15. The shift point of the cell condition is the characteristic point (for example, the peak point and the shift point).

Figure 5:
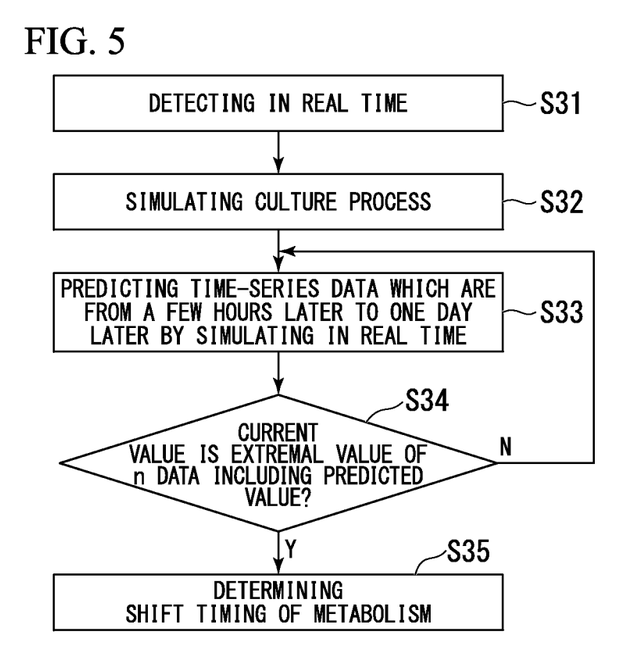
FIG. 5 is another example of a flowchart of determining a shift timing of the metabolism.

FIG. 5 is another example of a flowchart of determining a shift timing of the metabolism. In FIG. 5, the shift timing of the metabolism is determined as the shift timing of the cell condition. First, the simulator 17 detects the time-series data in real time (step S31). Next, the simulator 17 simulates a culture process (step S32). Thereafter, the simulator 17 calculates the time-series data which are from a few hours later to one day later by simulating in real time (step S33).

Next, the simulator 17 determines whether or not a current value is an extremal value of n data including the predicted value (step S34). In a case where the current value is not the extremal value (step S34: NO), processing returns to step S33. In a case where the current value is the extremal value (step S34: YES), the simulator 17 determines the shift timing of the metabolism as the shift timing of the cell condition (step S35).

<Control Value Setter 19>

Figure 7:
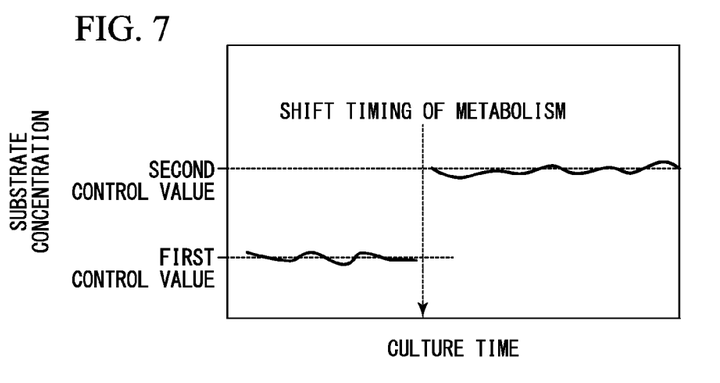
FIG. 7 is a graph illustrating a relation between the culture time and the substrate concentration.

The control value setter 19 is connected to the extractor 14. The control value setter 19 preliminarily stores a first control value and a second control value. The control value setter 19 also preliminarily stores an adding amount of the additives. When the extractor 14 outputs the characteristic point of the time-series data, the control value setter 19 determines the predetermined adding amount of the additives and switches the first control value to the second control value as shown in FIG. 7. The control value setter 19 is connected to an inputter B. The control value setter 19 changes the first control value, the second control value, and the adding amount of the additives.

<Controller 15>

The controller 15 is equipped with the additive controller 15a, the nutrient source controller 15b, the pH controller 15c, the osmotic pressure controller 15d, the gas flow controller 15e, the temperature controller 15f, and the agitation controller 15g.

(Additive Controller)

The additive controller 15a is connected to the control value setter 19. The additive controller 15a makes a first control unit 25a perform a supply operation and a block operation in accordance with the information (the adding amount of the additives) output from the control value setter 19. By this control, the additive controller 15a adds the additives (for example, the lactic acid and the ammonia) from a first supply source 35a to the culture fluid in the processor 10. In this way, the additive controller 15a controls the concentration value of the additives which exist in the culture fluid in the processor 10. For example, the first controller 25a is such as a valve and a flowmeter. The first control unit 25a may be controlled to be a middle-opened state other than a full-opened state and a closed state.

(Nutrient Source Controller 15b)

The nutrient source controller 15b is connected to the control value setter 19 and the sensor 11. The nutrient source controller 15b makes a second control unit 25b perform a supply operation and a block operation so as to make the concentration value of the nutrient sources detected by the sensor 11 correspond to the information (the control value) output from the control value setter 19. By this control, the nutrient source controller 15b adds the nutrient sources (for example, the glucose and the glutamine) from a second supply source 35b to the culture fluid in the processor 10. In this way, the nutrient source controller 15b controls the concentration value of the nutrient sources which exist in the culture fluid in the processor 10. For example, the second control unit 25b is such as a valve and a flowmeter. The second control unit 25b may be controlled to be a middle-opened state other than a full-opened state and a closed state.

(pH Controller 15c)

The pH controller 15c is connected to the control value setter 19 and the sensor 11. In a case where the pH value detected by the sensor 11 is lower than the information (control value) output from the control value setter 19, the pH controller 15c makes a third control unit 25c perform a supply operation and a block operation so as to add alkali solution (pH adjusting material) from a third supply source 35c to the culture fluid in the processor 10. By this control, the pH controller 15c makes the pH value of the culture fluid in the processor 10 be higher. To the contrary, in a case where the pH value detected by the sensor 11 is higher than the information (control value) output from the control value setter 19, the pH controller 15c makes a fifth control unit 25e perform a supply operation and a block operation so as to add $CO_2$ gas (pH adjusting material) from a fifth supply source 35e to the culture fluid in the processor 10. By this control, the pH controller 15c makes the pH value of the culture fluid in the processor 10 be lower. For example, the third control unit 25c and the fifth control unit 25e are such as a valve and a flowmeter. The third control unit 25c and the fifth control unit 25e may be controlled to be a middle-opened state other than a full-opened state and a closed state.

(Osmotic Pressure Controller 15d)

The osmotic pressure controller 15d is connected to the control value setter 19 and the sensor 11. The osmotic pressure controller 15d makes a fourth control unit 25d perform a supply operation and a block operation so as to make the osmotic pressure value detected by the sensor 11 correspond to the information (the control value) output from the control value setter 19. By this control, in a case where the control value is lower than the osmotic pressure value detected by the sensor 11, the osmotic pressure controller 15d adds natrium chloride (NaCl) from a fourth supply source 35d to the culture fluid in the processor 10. In this way, the osmotic pressure controller 15d controls the osmotic pressure of the culture fluid in the processor 10. For example, the fourth control unit 25d is such as a valve and a flowmeter. The fourth control unit 25d may be controlled to be a middle-opened state other than a full-opened state and a closed state.

(Gas Flow Controller 15e)

The gas flow controller 15e is connected to the control value setter 19 and the sensor 11. The gas flow controller 15e makes the fifth control unit 25e perform a supply operation and a block operation so as to make the concentration value of the dissolved oxygen detected by the sensor 11 correspond to the information (the control value) output from the control value setter 19. By this control, the gas flow controller 15e adds the gas (Air, $CO_2$, $N_2$, and so on) from the fifth supply source 35e to the culture fluid in the processor 10. For example, the fifth control unit 25e is such as a valve and a flowmeter. Because the fifth control unit 25e supplies various types of gas, it is preferable for the fifth control unit 25e to be equipped with the valve and the flowmeter. By this configuration, the fifth control unit 25e can control flow amount in a middle-opened state other than a full-opened state and a closed state.

(Temperature Controller 15f)

The temperature controller 15f is connected to the control value setter 19 and the sensor 11. The temperature controller 15f controls electrical power of a heater (temperature adjuster) so that the temperature value detected by the sensor 11 corresponds to the information (the control value) output from the control value setter 19. The heater (not shown) may be disposed inside the processor 10 (on the side of the culture fluid), and the heater may be disposed outside the processor 10.

(Agitation Controller 15g)

The agitation controller 15g is connected to the control value setter 19. The agitation controller 15g controls electrical power of a motor (not shown) for agitating the culture fluid in the processor 10 so that the electrical power of the motor corresponds to the information (the control value) output from the control value setter 19.

Figure 2:
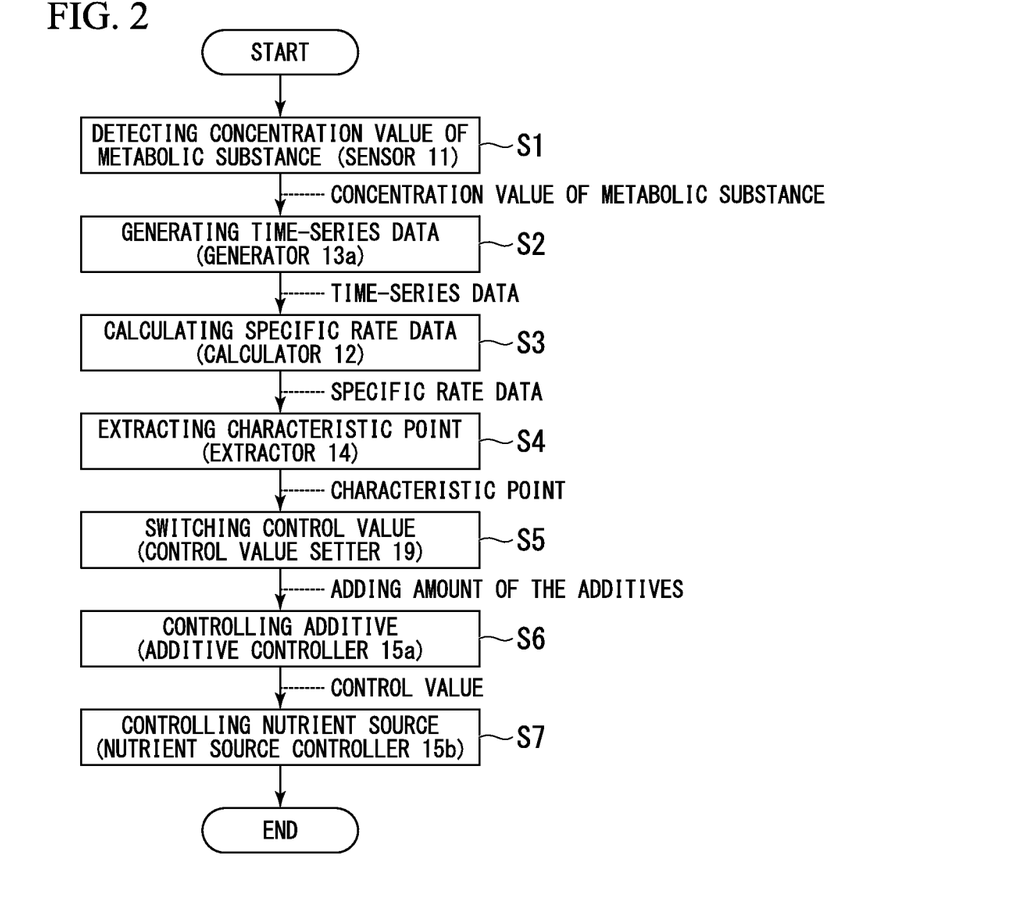
FIG. 2 is a flowchart illustrating a method of controlling the cell culture control system.

FIG. 2 is a flowchart illustrating a method of controlling the cell culture control system. The cell culture control system 1 of the present embodiment monitors the culture state (for example, the concentration of the each component in the culture fluid). The cell culture control system 1 keeps and manages a suitable culture condition. However, the flowchart shown in FIG. 2 is an example, and the present invention is not limited thereto.

The method of controlling the cell culture control system will be described below, with reference to the flowchart shown in FIG. 2. One or more programs for executing the each step of FIG. 2 are stored in a non-transitory computer readable storage medium. The sensor 11 detects the concentration value of the metabolic substances which exist in the culture fluid in the processor 10 (step S1). The sensor 11 outputs the information indicating the detected concentration value of the metabolic substances to the memory 13. The generator 13a in the memory 13 generates time-series data of the concentration value of the metabolic substances detected by the sensor 11 (step S2). The memory 13 stores the generated time-series data. The memory 13 outputs the stored time-series data of the concentration value of the metabolic substances to the calculator 12.

The calculator 12 calculates the specific production rate value of the metabolic substances in accordance with the time-series data of the concentration value of the metabolic substances stored in the memory 13 and the cell density detected by the sensor 11 (step S3). The calculator 12 stores time-series data of the calculated specific production rate value of the metabolic substances in the memory 13. The calculator 12 outputs the time-series data of the concentration value of the metabolic substances obtained from the memory 13 and the time-series data of the specific production rate value of the metabolic substances stored in the memory 13 to the extractor 14.

The extractor 14 extracts a characteristic point from the time-series data of the concentration value of the metabolic substances or the specific production rate value of the metabolic substances (step S4). The extractor 14 outputs the extracted characteristic point to the control value setter 19. The control value setter 19 switches the control value of the nutrient sources concentration from a first control value to a second control value (step S5). The control value setter 19 outputs the information (the new control value of the adding amount of the additives=the second control value) to the additive controller 15a.

The additive controller 15a makes the first control unit 25a perform the supply operation and the block operation in accordance with the information indicating the adding amount of the additives (the new control value of the adding amount of the additives=the second control value) obtained from the control value setter 19 (step S6). By this control, the additive controller 15a adds the additives (for example, the feed agents and the augmenting agents) from the first supply source 35a to the culture fluid in the processor 10. In this way, the additive controller 15a controls the concentration value of the additives which exist in the culture fluid in the processor 10 so that the concentration value of the additives correspond to the second control value.

In a case of using the predicted value which is calculated by the simulator 17, the adding amount of the nutrient components is calculated so that a difference between the control value of the concentration and the predicted value can be approximately zero. Information corresponding to the calculated adding amount is output to an adding pump (not shown) corresponding to the first control unit 25a and the first supply source (additive) 35a.

In a case where a signal indicating a cell condition shift is input from the extractor 14, the control value setter 19 sequentially switches the control values of the concentration. Further, when the signal is input from the extractor 14 to the control value setter 19, the control value setter 19 outputs a signal, which is a signal according to a predetermined adding amount of the additives, to the adding pump (not shown) corresponding to the first control unit 25a and the first supply source (additive) 35a.

The nutrient source controller 15b makes the second control unit 25b perform the supply operation and the block operation in accordance with the information (the new control value of the adding amount of the additives=the second control value) obtained from the control value setter 19 (step S7). By this control, the nutrient source controller 15b adds the nutrient sources (for example, the glucose and the glutamine) from the second supply source 35b to the culture fluid in the processor 10. In this way, the nutrient source controller 15b controls the concentration value of the nutrient sources which exist in the culture fluid in the processor 10.

As is the case with the additive controller 15a, there are three cases with respect to the nutrient source controller 15b. A first case is a case that the value detected by the sensor 11 or the value calculated by the calculator 12 is lower than the predetermined control value of the concentration [a predetermined control value (target value) which is a physical and chemical parameter of the culture fluid in the processor 10]. A second case is a case of using the predicted value which is calculated by the simulator 17. A third case is a case that the signal of the cell condition shift is input from the extractor 14. In any of these cases, as is the case in the additive controller 15a, the control value is set so that the nutrient source controller 15b can function.

An operation of the cell culture control system will be described below.

<Lactic Acid Case>

Figure 8:
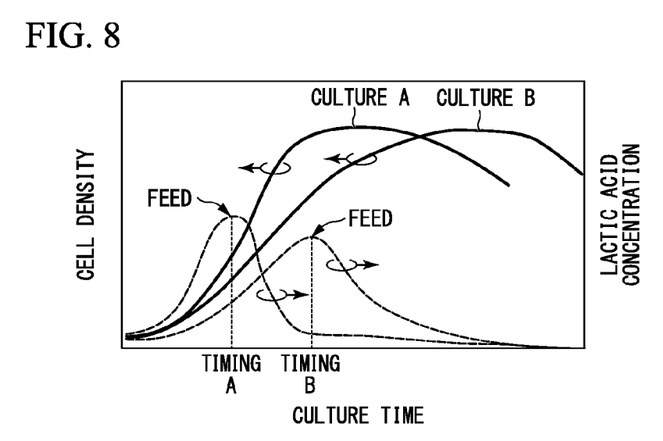
FIG. 8 is a graph illustrating an example of a relation between the culture time and the cell density and the lactic acid concentration.
Figure 9:
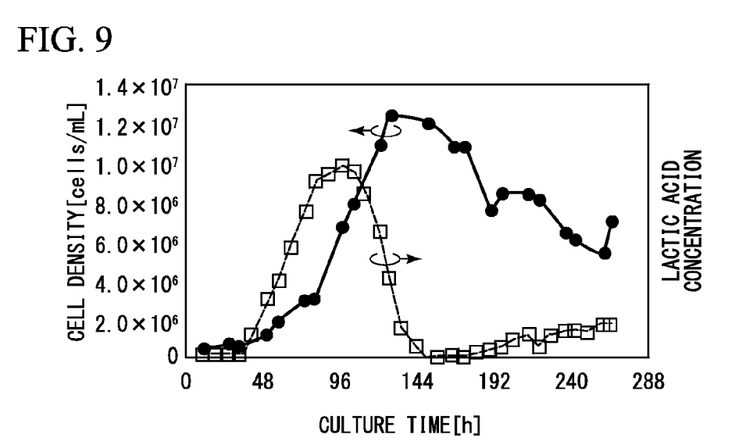
FIG. 9 is a graph illustrating another example of a relation between the culture time and the cell density and the lactic acid concentration.

In a case where the cells in the culture fluid in the processor 10 grow, (in other words, in a case where the cell density increases), the lactic acid increases. In accordance with the increase of the lactic acid, the output value from the sensor 11 increases, the time-series data stored in the memory 13 increases. The specific production rate of the lactic acid calculated by the calculator 12 is a positive value. Because the inclination of the time-series data is not shifted, the extractor 14 does not output the characteristic point of the time-series data to the control value setter 19. As the result, the control value setter 19 holds the first control value. Therefore, the additive controller 15a operates in accordance with the first control value (FIG. 6, FIG. 8, and FIG. 9).

When the lactic acid decreases after the lactic acid had increased, the output from the sensor 11 decreases. Because the time-series data stored in the memory 13 decreases in accordance with the decrease of the output from the sensor 11, the specific production rate of the lactic acid is a negative value. Therefore, the extractor 14 determines the time when the sign of the time-series data is shifted as the characteristic point (the peak point or the shift point). The control value setter 19 switches from the first control value to the second control value. Therefore, the additive controller 15a switches from an operation based on the first control value to an operation based on the second control value.

<Ammonia Case>

As is the case with the lactic acid, in a case where the cells in the culture fluid in the processor 10 grow, (in other words, in a case where the cell density increases), the ammonia increases. In accordance with the increase of the ammonia, the output value from the sensor 11 increases, and the time-series data stored in the memory 13 increases. The specific production rate of the ammonia calculated by the calculator 12 is a positive value. Because the inclination of the time-series data is not shifted, the extractor 14 does not output the characteristic point of the time-series data to the control value setter 19. As the result, the control value setter 19 holds the first control value. Therefore, the nutrient source controller 15b operates in accordance with the first control value (FIG. 6, FIG. 8, and FIG. 9).

When the time-series data of the ammonia concentration is shifted, the output from the sensor 11 is also shifted. In accordance with the shift, the time-series data stored in the memory 13 is shifted. The extractor 14 extracts the time when the sign of the time-series data shifts as the characteristic point (the peak point or the shift point). The characteristic point extracted by the extractor 14 is a shift point of a trend of the concentration value of the ammonia. The control value setter 19 switches from the first control value to the second control value. Therefore, the nutrient source controller 15b switches from an operation based on the first control value to an operation based on the second control value.

In any cases of the lactic acid and the ammonia, an operator looks at the display 8 and changes the control value by using the inputter B. In a case where the cell density or the survival rate exceeds a predetermined range, the operator inputs a new control value. Although it is described that the operator changes the control value, this is not a restriction. For example, the cell culture control system 1 may be established so that, instead of the operator, a computer changes the control value and inputs a new control value based on a predetermined rule.

Keywords according to the present embodiment will be described below.

<Cell Condition and Shift Thereof>

The "cell condition" in the present embodiment is such as a growth rate per one cell and a condition of energetic metabolism (for example, the specific growth rate, the specific consumption rate of the nutrient components, and the specific production rate of the metabolic substance), and a parameter represented by a biotic factor indicating a productivity of target protein and their ratio. Generally, the specific rates and the parameters are detected once or twice a day by an offline analysis, and approximately calculated by using an integral approach or the like.

For the reason, the number of the data is few. The calculated value is obtained as a past value which is averaged from every half a day to every day. Although the concentration value of the metabolic substance is likely to increase in the culture fluid generally, for example, the lactic acid shifts from a state of being produced to a state of being consumed in accordance with the cell condition (metabolic state). For example, the information is described in Woo Suk Ahn, Maciek R. Antoniewicz, Metabolic Engineering 13 (2001): 598-609, Wei Shou Hu, "CELL CULTURE BIOPROCESS ENGINEERING": 236 (book), and so on.

<Adding the Feed Agent>

Generally, the feed agents and the augmenting agents are added for the sake of replenishing the nutrient source which lacks while culturing, adding components for increase the growth rate and the productivity, and attenuating the accumulated waste material. However, the adding timing of the feed agents and the augmenting agents is not determined. Generally, a user mixes a simple or plural feed agent into the culture fluid, and the user determines the adding timing by calculating a condition in accordance with an indicator such as a culture time (number of days) and the number of the cells.

So as to improve the productivity, it is desirable that the energy is used for increasing the cells as much as possible in a growth phase, and the energy is used for producing the objective products in a production phase or later. For the reason, appropriate concentration of the culture medium components in the growth phase is different from appropriate concentration of the culture medium components in the production phase or later, and the components are added while culturing. However, because the cell culture has a biological-induced variability, the cell growth situations (aging variations of the cell condition) between batches are not always the same. Therefore, if the feed timing is determined in accordance with the culture time and the number of the cells, there is a case that it is difficult to add in accordance with the cell condition.

<Osmotic Pressure>

The osmotic pressure is an important environmental factor. The osmotic pressure control can be implemented by controlling the feed of the nutrient source, NaCl, and so on. A relation between the glucose concentration and the osmotic pressure (detected by a freezing point depression method) in the batch culture (the glucose is added as shot-addition) is shown in FIG. 6. As shown in FIG. 6, the trend of the osmotic pressure approximately depends on the trend of the glucose trend, and the osmotic pressure can be controlled by the feed control. An early osmotic pressure in the culture fluid is generally controlled so as to approximately correspond to an osmotic pressure of isotonic fluid (about 280 [osmol/Kg]). In the isotonic fluid, concentration of materials which cannot pass through a semipermeable membrane corresponds to concentration of fluid in the cells. However, with the progression of culturing, the osmotic pressure is varied by adding the alkali solution and the nutrient sources, the metabolism of the cells, and so on. For example, effects of the osmotic pressure on the growth of the cells and the production of the antibody are described in Young Kue Han, et al., Biotechnology Bioengineering, 2010, Apr., 15; 105(6): 1187-1192, Moon Sue Lee, Gyun Min Lee, Cytotechnology, 2001, 36: 61-69, Duan Shen, et al., Biotechnol. Prog., 2010, Jul-Aug; 26(4): 1104-15, and so on.

<NIRS>

The NIRS (near-infrared (NIR) spectroscopy) is a dispersing method near-infrared region. The NIRS is a method of irradiating infrared-rays and calculating components of a detection target in accordance with a change of absorbance of the each wavelength component. Although the absorbance caused by a molecular vibration of components included in the detection target is used, because harmonic overtone is observed in the NIRS, an absorption spectrum is complicated by various factors.

However, in comparison with mid-infrared rays and far-infrared rays, in a case of the near-infrared rays, because absorption amount of water which is an obstacle for the analysis is very small, the NIRS is suitable for measuring fluid such as the culture fluid. By preliminarily creating a standard curve which associates the each component value with the absorbance, many components can be analyzed at a single measurement, and it is suitable for measuring the nutrient components and the metabolic components in the culture fluid in the present embodiment.

Because the cells in the culture fluid scatters light of measurement wavelength region, it contributes to a base line shift of the absorption spectrum. By taking advantage of this and detecting the relation of the number of the cells and the base line shift, the number of the cells can be simultaneously counted. Further, by taking advantage of the water absorption region in the spectrum, the osmotic pressure which is one of important environmental factors in the culture can be measured. The osmotic pressure is proportional to mol concentration of dissolved substances. In a case where an amount of the dissolved substances is varied, a ratio of water in the measurement area through which the light passes is likely to be varied, and a peak value in the absorption region is likely to be varied. For example, in a case where the amount of the dissolved substances is increased, the ratio of water in the measurement area is decreased, and the peak value in the absorption region goes down.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

As used herein, the following directional terms "forward, rearward, above, downward, right, left, vertical, horizontal, below, transverse, row and column" as well as any other similar directional terms refer to those directions of an apparatus equipped with the present invention. Accordingly, these terms, as utilized to describe the present invention should be interpreted relative to an apparatus equipped with the present invention.

The term "configured" is used to describe a component, unit or part of a device includes hardware and/or software that is constructed and/or programmed to carry out the desired function.

Moreover, terms that are expressed as "means-plus function" in the claims should include any structure that can be utilized to carry out the function of that part of the present invention.

The term "unit" is used to describe a component, unit or part of a hardware and/or software that is constructed and/or programmed to carry out the desired function. Typical examples of the hardware may include, but are not limited to, a device and a circuit.

What is claimed is:

1. A cell culture control system comprising:
   a control unit configured to control a supply operation of supplying additives to a tank for containing a culture fluid in which cells are cultured, the additives being feed agents or augmenting agents;
   a controller configured to control the control unit to control parameters of the culture fluid which exists in the tank in accordance with a control value which is preliminarily set;

a sensor configured to detect a cell density, a concentration value of metabolic substances, and a concentration value of nutrient sources in the culture fluid which exists in the tank by using near-infrared spectroscopy;

a calculator configured to calculate a specific rate of the cell density, a specific rate of the concentration value of the metabolic substances, and a specific rate of the concentration value of the nutrient sources based on the cell density, the concentration value of the metabolic substances, and the concentration value of the nutrient sources detected by the sensor;

a generator configured to generate time-series data in accordance with the specific rate of the cell density, the specific rate of the concentration value of the metabolic substances, and the specific rate of the concentration value of the nutrient sources calculated by the calculator;

an extractor which comprises a simulator configured to calculate a predicted value of the time-series data in accordance with the time-series data generated by the generator, the extractor being configured to extract a characteristic point of the time-series data or a characteristic point of the predicted value, the characteristic point being a peak point or a shift point of the time-series data or the predicted value; and a control value setter configured to change the control value in accordance with the characteristic point extracted by the extractor, wherein the control value setter is configured to determine an adding amount of additives to be added to the tank based on an adding amount of additives stored in the control value setter at a timing of an output from the extractor, and wherein the controller is configured to control the control unit to supply the additives to the tank in accordance with the adding amount of the additives determined by the control value setter.

2. The cell culture control system according to claim 1, wherein in a case where the cells in the culture fluid grow, lactic acid increases, the sensor is configured to detect a concentration value of the lactic acid in the culture fluid, the calculator is configured to calculate a specific production rate of the lactic acid in accordance with the concentration value of the lactic acid detected by the sensor, a sign of the specific production rate of the lactic acid is shifted from positive to negative at a shift point, the extractor is configured to extract the shift point as the characteristic point, and the control unit is configured to add feed agents or augmenting agents into the culture fluid as the additives in accordance with the shift point extracted by the extractor.

3. The cell culture control system according to claim 1, wherein the sensor is configured to detect a concentration value of ammonia in the culture fluid, the extractor is configured to output a shift point of a trend of the concentration value of the ammonia detected by the sensor as the characteristic point, and the control unit is configured to add feed agents or augmenting agents into the culture fluid as the additives in accordance with the output from the extractor.

4. The cell culture control system according to claim 1, wherein the control value setter is configured to switch the control value from a first control value to a second control value at a timing of outputting from the extractor, and the controller is configured to control the control unit, which is disposed between a supply source of the additives and the tank, perform a supply operation and a block operation in accordance with the second control value switched by the control value setter.

5. The cell culture control system according to claim 4, wherein the control value corresponds to the concentration value of the nutrient sources detected by the sensor, and the control unit is configured to add the nutrient sources into the culture fluid in accordance with the output from the extractor, and make the concentration value of the nutrient sources correspond to the second control value.

6. The cell culture control system according to claim 4, wherein the sensor is configured to detect a pH value of the culture fluid which exists in the tank, the control value corresponds to the pH value of the culture fluid detected by the sensor, and the control unit is configured to add pH adjusting material into the culture fluid in accordance with the output from the extractor, and make the pH value of the culture fluid correspond to the second control value.

7. The cell culture control system according to claim 6, wherein in a case where the pH value detected by the sensor is lower than the second control value, the control unit adds alkali solution as the pH adjusting material into the culture fluid, in a case where the pH value detected by the sensor is higher than the second control value, the control unit adds $CO_2$ gas as the pH adjusting material into the culture fluid.

8. The cell culture control system according to claim 4, wherein the sensor is configured to detect an osmotic pressure value of the culture fluid which exists in the tank, the control value corresponds to the osmotic pressure value of the culture fluid detected by the sensor, and the control unit is configured to add osmotic pressure adjusting material into the culture fluid in accordance with the output from the extractor, and make the osmotic pressure value of the culture fluid correspond to the second control value.

9. The cell culture control system according to claim 8, wherein in a case where the second control value is lower than the osmotic pressure value of the culture fluid detected by the sensor, the control unit adds natrium chloride as the osmotic pressure adjusting material into the culture fluid.

10. The cell culture control system according to claim 4, wherein the sensor is configured to detect a temperature value of the culture fluid which exists in the tank, the control value corresponds to the temperature value of the culture fluid detected by the sensor, and the control unit is configured to control a temperature adjuster in accordance with the output from the extractor, and make the temperature value of the culture fluid correspond to the second control value.

11. The cell culture control system according to claim 4, wherein the sensor is configured to detect a concentration value of dissolved oxygen of the culture fluid which exists in the tank, the control value corresponds to the concentration value of the dissolved oxygen of the culture fluid detected by the sensor, and the control unit is configured to control a gas flow adjuster in accordance with the output from the extractor, and make the concentration value of the dissolved oxygen of the culture fluid correspond to the second control value.

12. The cell culture control system according to claim 1, wherein the calculator comprises an averager configured to calculate a representative value by averaging the output from the sensor in a predetermined period, and the averager calculates a rate component of the representative value based on the representative value calculated by the calculator.

13. The cell culture control system according to claim 1, wherein the sensor is configured to detect a pH value, a temperature value, a concentration value of dissolved oxygen, and an osmotic pressure value of the culture fluid which exists in the tank, and the extractor comprises a simulator configured to calculate a predicted value of the time-series data based on the time-series data generated by the generator, and extracts a characteristic point of the predicted value based on the predicted value calculated by the simulator.

14. The cell culture control system according to claim 1, wherein the generator is configured to generate the time-series data in accordance with the concentration value of the nutrient sources, store the generated time-series data, and store the characteristic point of the time-series data.

15. The cell culture control system according to claim 14, further comprising:

a display configured to display the time-series data of the concentration value of the nutrient sources, the time-series data of the concentration value of the metabolic substances, and the characteristic point, and an inputter connected to the control value setter and configured to input the control value to the control value setter.

16. The cell culture control system according to claim 1, wherein the controller controls electrical power of a motor for agitating the culture fluid which exists in the tank in accordance with the control value output from the control value setter.

17. A cell culture control method for controlling the cell culture control system according to claim 1, the cell culture control method comprising:

controlling, by the control unit, the supply operation of supplying additives to the tank for containing the culture fluid in which cells are cultured, the additives being feed agents or augmenting agents;

controlling, by the controller, the control unit to control parameters of the culture fluid which exists in the tank in accordance with a control value which is preliminarily set;

detecting, by the sensor, the cell density, the concentration value of metabolic substances, and the concentration value of nutrient sources in the culture fluid which exists in the tank by using near-infrared spectroscopy;

calculating, by the calculator, the specific rate of the cell density, the specific rate of the concentration value of the metabolic substances, and the specific rate of the concentration value of the nutrient sources based on the cell density, the concentration value of the metabolic substances, and the concentration value of the nutrient sources detected by the sensor;

generating, by the generator, time-series data in accordance with the specific rate of the cell density, the specific rate of the concentration value of the metabolic substances, and the specific rate of the concentration value of the nutrient sources calculated by the calculator;

calculating, by the simulator, the predicted value of the time-series data;

extracting, by the extractor, the characteristic point of the time-series data or the characteristic point of the predicted value, the characteristic point being the peak point or the shift point of the time-series data or the predicted value;

changing, by the control value setter, the control value in accordance with the characteristic point extracted by the extractor;

determining, by the control value setter, an adding amount of additives to be added to the tank based on an adding amount of additives stored in the control value setter at a timing of an output from the extractor, and controlling, by the controller, the control unit to supply the additives to the tank in accordance with the adding amount of the additives determined by the control value setter.

18. A non-transitory computer readable storage medium storing one or more programs configured for execution by a computer, the one or more programs comprising instructions for performing the cell culture control method according to claim 17.

* * * * *